United States Patent [19]

Hershenson et al.

[11] Patent Number: 4,894,330

[45] Date of Patent: Jan. 16, 1990

[54] PURIFICATION OF RECOMBINANT BETA-INTERFERON INCORPORATING RP-HPLC

[75] Inventors: Susan Hershenson, San Francisco; Ze'ev Shaked, Berkeley, both of Calif.

[73] Assignee: Cetus Corporation, Emeryville, Calif.

[21] Appl. No.: 946,083

[22] Filed: Dec. 23, 1986

[51] Int. Cl.[4] .................... C12P 21/00; A61K 45/02; C07K 15/26

[52] U.S. Cl. ................................ 435/69.51; 530/351; 424/85.6

[58] Field of Search ........................... 435/65; 424/85; 530/351

[56] References Cited

U.S. PATENT DOCUMENTS

| | | | |
|---|---|---|---|
| 4,289,689 | 9/1981 | Friesen et al. | 424/85 |
| 4,289,690 | 9/1981 | Pestka et al. | 424/85 |
| 4,343,735 | 8/1982 | Menge et al. | 424/85 |
| 4,462,940 | 7/1984 | Hanisch et al. | 424/85 |
| 4,485,017 | 11/1984 | Tan et al. | 424/85 |
| 4,569,790 | 2/1986 | Koths et al. | 424/85 |
| 4,617,378 | 10/1986 | Rubinstein et al. | 424/85 |
| 4,748,234 | 5/1988 | Doren et al. | 530/412 |

FOREIGN PATENT DOCUMENTS

| | | |
|---|---|---|
| 206828 | 12/1986 | European Pat. Off. . |
| 235077 | 4/1986 | German Democratic Rep. . |
| 2055384 | 3/1981 | United Kingdom . |

OTHER PUBLICATIONS

Tarr et al., *Analyt. Biochem.*, 131:99–107 (1983).
Heukeshoven et al., *Chromatographia*, 19:95–100 (1985).
Bennett et al., *Biochem. J.*, 197:391–400 (1981).
Moshera et al., *Texas Reports on Biology and Medicine*, 41:250–259 (1981–1982).
Stein, *Trends in Analyt. Chemistry*, 3(4):99–101 (1984).
Ray et al., 613th Meeting, Cardiff (vol. 13), pp. 1233–1234.
Kunitani et al., *J. Chromatography*, 359:391–402 (1986).
Pestka et al., *Pharmac. Ther.*, 29:299–319 (1985).
Langer et al., *J. Investig. Dermatol.*, 83 (1):128S–136S (1984).
Pestka et al., *Archives Biochem. Biophys.*, 221(1):1–37 (1983).
Bennett et al., *Biochem.*, 20:4530–4538 (1981).
Burgess et al., *PNAS*, 79:5753 (1982).
Smith-Johannsen et al., *J. Ifn. Res.*, 3(4):473–477 (1983).
Colby et al., *J. Immunol.*, 133(6)3091–3095 (1984).
Freisen in Molnar (ed.), *Practical Aspects of Modern HPLC* (Proceedings Dec. 7–8, 1981 in West Berlin):-77–107.
Freisen et al., *Arch. Biochem. Biophys.*, 206(2):432–450 (1981).
Pasechnik, *J. Chromatography*, 364:359–368 (1986).
Guiochon et al., *Chromatography Forum*, pp. 21–28 (Sep.–Oct. 1986).

*Primary Examiner*—Blondel Hazel
*Attorney, Agent, or Firm*—Philip L. McGarrigle; Janet E. Hasak; Albert P. Halluin

[57] ABSTRACT

Improved RP-HPLC methods for purifying recombinant betainterferon are disclosed. Said RP-HPLC methods employ wide pore silica gel reverse-phase columns and solvent systems containing acetonitrile as the organic modifier and either heptafluorobutyric acid or trifluoroacetic acid as the organic acid.

The invention further concerns processes for purifying recombinant IFN-$\beta$ incorporating said improved RP-HPLC methods.

The invention further concerns recombinant IFN-$\beta$ purified by said RP-HPLC methods, or recovered and/or purified by processes incorporating said RP-HPLC.

34 Claims, No Drawings

PURIFICATION OF RECOMBINANT BETA-INTERFERON INCORPORATING RP-HPLC

FIELD OF THE INVENTION

This invention is in the field of biochemical engineering. More particularly, the invention concerns reverse-phase high performance liquid chromatography (RP-HPLC) methods for purifying recombinant beta-interferon (IFN-$\beta$), and improved processes for purifying recombinant IFN-$\beta$ incorporating said RP-HPLC methods. Said processes result in increased purity and decreased heterogeneity of the product.

BACKGROUND OF THE INVENTION

Naturally occurring interferons (IFNs) are species-specific proteins, often glycoproteins, produced by various cells upon induction with viruses, double stranded RNAs, other polynucleotides, antigens and mitogens. Interferons exhibit multiple biological activities such as antiviral, antiproliferative, immunomodulatory and anticellular functions. At least three distinct types of human interferons have been indentified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

Native human $\beta$-interferon is generally produced by superinducing human fibroblast cultures with poly-IC (polyriboinosinic acid and polyribocytidylic acid) and isolating and purifying native human $\beta$-interferon thus produced by chromatographic and electrophoretic techniques. Proteins or polypeptides which exhibit native $\beta$-interferon-like properties may also be produced using recombinant DNA technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the IFN-$\beta$ therefrom. Nagola, S. et al., Nature, 284: 316 (1980); Goeddel, D. V. et al., Nature, 287: 411 (1980); Yelverton, E. et al., Nuc. Acid Res., 9: 731 (1981); Streuli, M. et al., Proc. Nat'l. Acad. Sci. (U.S.), 78: 2848 (1981); European Pat. Application Nos. 28033, published May 6, 1981; 321134, published July 15, 1981; 34307 published Aug. 26, 1981; and Belgian Patent 837397, issued July 1, 1981 describe various currently used methods for the production of $\beta$-interferon employing recombinant DNA techniques. The expressed proteins or polypeptides have been purified and tested and have been found to exhibit properties similar to those of native IFNs. Bacterially produced IFNs thus appear to have potential therapeutic use as antiviral and anti-tumor agents and the production of IFNs by such bacterial fermentations is expected to yield sufficiently large quantities of IFN at a relatively low cost of clinical testing.

Further, human IFN-$\beta$ genes have been altered by, for example, oligonucleotide-directed mutagenesis to produce IFN-$\beta$ protein analogs thereof, such as the human recombinant cysteine-depleted or cysteine-replaced interferon-$\beta$ analogs (muteins) disclosed in U.S. Pat. No. 4,588,585 issued May 13, 1986 to Mark et al. Specifically disclosed in that patent is the recombinant IFN-$\beta$ wherein the cysteine at position 17 is replaced by the neutral amino acid serine. That IFN-$\beta$ analog is IFN-$\beta_{ser17}$.

Procedures for recovering and purifying bacterially produced IFNs are described in U.S. Pat. Nos. 4,450,103; 4,315,852; 4,343,735; and 4,343,736; and Derynck et al., Nature (1980) 287: 193–197 and Scandella and Kornberg, Biochemistry, 10: 4447 (1971). Generally with these methods the IFN is not produced in a sufficiently pure form and in sufficiently large quantities for clinical and therapeutic purposes and the resulting IFN preparations produced by recombinant DNA techniques have residual amounts of chemicals and considerable microheterogeneity.

Purification and activity assurance of precipitated heterologous proteins is also described by U.S. Pat. Nos. 4,511,502; 4,511,503; 4,512,922; and 4,518,526; and in European Patent 114,506.

Copending, commonly owned U.S. patent application Ser. No. 843,997 filed Mar. 25, 1986 entitled "Process for Recovering Refractile Bodies Containing Heterologous Proteins from Microbial Hosts" discloses a biochemical separation or recovery process in which refractile bodies containing microbially produced IFN-$\beta$ are separated or recovered from the microorganism hosts, and further discloses protocols for then purifying the isolated refractile bodies or refractile material.

Commonly owned U.S. Pat. No. 4,462,940, and copending commonly owned U.S. patent application Ser. Nos. 775,751 (filed Sept. 13, 1985), 923,425 (filed Oct. 27, 1986) and 923,432 (filed Oct. 27, 1986) further disclose processes for purifying and formulating recombinant IFN-$\beta$.

U.S. Pat. No. 4,343,735 to Menge et al. teaches a process for the purification of interferon by partitioning it in an aqueous multi-phase system in the presence of ion exchangers which are soluble in the system and are derivatives of polyethers.

U.S. Pat. No. 4,289,690 to Pestka et al. discloses processes for purifying proteins including native human leukocyte interferon by utilizing one or more high performance liquid chromatography steps employing as solvents alkanols, such as n-propanol. See also, Pestak et al., Pharmac. Ther., 29: 299–319 (1985); Langer et al., J. Investig. Dermatol., 83 (1): 1285–1365 (1984); and Pestka, S., Archives Biochem. Biophys., 221 (1): 1–37 (Feb. 15, 1983).

U.S. Pat. No. 4,289,689 to Friesen et al., discloses how to recover and purify human native $\beta$-interferon by use of affinity chromatography and high pressure liquid chromatography.

In handling a biologically active protein, such as recombinant IFN-$\beta$, general considerations concerning the handling of proteins are relevant, including the necessity of preserving the protein's delicate tertiary structure in order to preserve biological activity, which requires the avoidance of denaturing pH conditions. E. coli expressed recombinant IFN-$\beta$ and analogs thereof are insoluble in solutions which are at a pH range of 6 to 9. Therefore, various processes and additives have been devised to solubilize these proteins.

In producing a recombinant protein such as IFN-$\beta$ which is to be administered therapeutically to humans or animals, considerations of purity and homogeneity of the final product are of the utmost concern. Reduction or elimination of minor IFN-$\beta$ species, and removal of both non-IFN-$\beta$ proteins and bacterial endotoxins, are of prime importance. Secondarily, in establishing or improving a purification scheme of a therapeutic, recombinant protein are considerations of efficiency and simplicity of the process.

The variations on the theme of protein purification have been explored for more than fifty years. The literature on this subject is extensive and a plethora of techniques is available to the practitioner, including ion exchange chromatography, adsorption chromatography, gel electrophoresis, ammonium sulfate precipitations, and gel filtration. Over the years there have been substantial improvements in the technology of conducting many of the foregoing methods, and in particular, it has been possible to automate and speed up the procedures related to column chromatography and development of electrophoresis gels. Despite these technical advances, and despite the large number of proteins which have been subjected to these procedures, the selection of a successful procedure, or more usually combination of procedures, for a particular protein found in a particular milieu has remained unpredictable, unselectable in advance, and subject to considerable experimentation in each particular case.

The instant invention incorporates a RP-HPLC method, specifically adapted for the purification of recombinant IFN-$\beta$, in purification processes essentially outlined in commonly owned, copending U.S. patent application Ser. Nos. 843,997 (filed Mar. 25, 1986) and 923,423 (filed Oct. 27, 1986), which applications are herein incorporated by reference. References to purification schemes for recombinant proteins also employing RP-HPLC are listed below.

U.S. Pat. No. 4,485,017 issued to Tan et al. discloses a process for the isolation and purification of native interferons wherein a partially purified preparation of native interferon is sequentially passed through an antibody affinity column and an RP-HPLC column.

U.S. Pat. No. 4,569,790 issued to Koths et al. discloses a process for recovering microbially produced IL-2 wherein the oxidized IL-2 is purified by RP-HPLC. A gradient solvent system comprising an organic acid such as acetic acid or trifluoroacetic acid (TFA) and an organic solvent such as propanol or acetonitrile is used to elute the IL-2 from the reverse-phase column.

Tarr et al., *Anal. Biochem.*, 131: 99–107 (1983) describes the use of RP-HPLC resolution and recovery of cytochrome P-450 and bovine rhodopsin using ternary solvents, including acetonitrile and n-propanol and mixtures of the two.

Bennett et al., *Biochem.*, 20: 4530–4538 (1981) describes the purification of two major forms of rat corticotropin (ACTH) to apparent homogeneity by RP-HPLC using solvent systems containing either TFA or heptafluorobutyric acid (HFBA) as hydrophobic counter-ions.

Bennett et al., *Biochem.*, 197: 391–400 (1981) describes the isolation and analysis of human parathyrin wherein RP-HPLC employing solvent systems composed of aqueous acetonitrile containing TFA or HFBA as hydrophobic ion-pairing reagents is used.

Smith-Johannsen et al., *J. IFN. Res.*, 3 (4): 473–477 (Nov. 4, 1983) discloses a procedure involving the chromatography of native human IFN-$\beta$ on an antibody affinity column followed by RP-HPLC. The RP-HPLC was performed wherein the elution solvent contained n-propanol in a linear gradient of between 0–100%, and wherein the $C_{18}$ column was equilibrated with 100 mM formic acid. See also, Colby et al., *J. Immunol.*, 133 (6): 3091–3095 (December, 1984) wherein recombinant IFN-$\beta$ is purified according to the Smith-Johannsen et al. method.

Heukeshoven et al., *Chromatographia*, 19: 95–100 (1985) discloses RP-HPLC for various virus proteins and other hydrophobic proteins wherein a proportion of 60% formic acid in all solvents was used and wherein 2-propanol or acetonitrile was the organic modifier for gradient elution.

Burgess et al., *PNAS* (USA), 79: 5753–5757 (October 1982) discloses the separation of two forms of murine 1982) epidermal growth factor by using RP-HPLC wherein the results of employing solvent systems containing either 0.2% trifluoroacetic acid or 0.2% heptafluorobutyric acid and 20 or 50% acetonitrile were compared.

Friesen et al., *Arch. Biochem. Biophys.*, 206 (2):432–450 (February 1981) discloses the purification of native human IFN-$\beta$ by a combination of affinity chromatography and RP-HPLC wherein the reverse-phase column is equilibrated with pyridine-formic acid containing isopropanol and/or n-butanol.

Molnar (Ed.), *Practical Aspects of Modern HPLC* (Proceedings Dec. 7–8, 1981 in West Berlin): Freisen, H., "HPLC of Protein on Reverse Phase Exemplified with Human Interferons and Other Proteins: Review and Scope of a Method" (pp. 77–107) provides a review article on reverse phase chromatography of proteins, including interferons.

The instant invention provides improved purification processes incorporating RP-HPLC methods specific for recombinant IFN-$\beta$. Said processes produce a highly pure IFN-$\beta$ product at very reduced levels of minor IFN-$\beta$ species, bacterial endotoxins and non-IFN-$\beta$ proteins. Said processes provide flexible options for simplifying and improving the efficiency of the purification of recombinant IFN-$\beta$, as well as increasing the purity and homogeneity of the product.

SUMMARY OF THE INVENTION

In one aspect, the present invention relates to improved RP-HPLC methods of purifying recombinant IFN-$\beta$. In another aspect, the invention concerns processes of purifying recombinant IFN-$\beta$ incorporating one or more of said RP-HPLC methods. Said purification processes provide for increased purity and decreased heterogeneity of the recombinant IFN-$\beta$ product.

Said RP-HPLC methods comprise using bonded phase wide pore silica gel columns, and solvent systems containing acetonitrile as an organic modifier and either heptafluorobutyric acid (HFBA) or trifluoroacetic acid (TFA) as the organic acid.

The bonded phase wide pore silica gel columns are preferably alkane reverse phase columns, more preferably $C_4$, $C_8$ or $C_{18}$ columns. When TFA is the acid used in the solvent system a $C_4$ column is preferred. Whereas, when HFBA is the acid chosen, a $C_{18}$ column is preferred. The pore-size of said silica gels is preferably 300 angstroms or larger.

The elution can be either isocratic or gradient, preferably gradient, either linear or non-linear, wherein the concentration (v/v) of acetonitrile is in a range from 0% to 100%, preferably from 50% to about 80%, and more preferably from 50% to about 65%. The slope of the gradient elution is preferably balanced with the amount of material loaded on the reverse phase column. The HFBA or TFA in the elution solvent system is in a concentration range of from about 0.001% to about 2%, preferably from about 0.05% to about 1%, and more preferably from about 0.1% to about 0.2%.

The most preferred RP-HPLC method of this invention comprises employing a $C_{18}$ reverse-phase column with an elution solvent containing acetonitrile as the organic modifier in a gradient of from about 50% to about 65%, and HFBA in a concentration of about 0.1%.

The invention further provides processes for purifying recombinant IFN-$\beta$ incorporating said improved RP-HPLC methods.

Another aspect of this invention concerns recombinant IFN-$\beta$ purified by the RP-HPLC methods of this invention and IFN-$\beta$ recovered and/or purified by the processes incorporating said RP-HPLC methods.

DETAILED DESCRIPTION OF THE PREFERRED EMBODIMENTS

As indicated above in the Background, there are a number of processes for recovering recombinantly produced IFN-$\beta$. The RP-HPLC methods of the invention may be incorporated therein.

Preferred purification processes of the instant invention include those described in copending, commonly owned U.S. patent application Ser. Nos. 843,997 (filed Mar. 25, 1986) 923,423 (filed Oct. 27, 1986) and 923,425 (filed Oct. 27, 1986), wherein the RP-HPLC methods of the instant invention are incorporated. Those patent applications are herein incorporated by reference. Protocols 1 through 3, below, illustrate such preferred processes wherein the RP-HPLC methods can be incorporated. Such protocols schematically illustrate preferred processes for recovering, purifying and formulating microbially produced IFN-$\beta$.

| PROTOCOL 1 | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15–23% sucrose (w/w) |
| Centrifugation | 10,000–15,000 × g |
| Paste solubilization | 2% SDS, phosphate buffered saline |
| Reduction | 10 mM DTT; 2% SDS; 2mM EDTA; pH 9; heat to 50° C. for 10 min. under nitrogen; cool to about 25° C. adjust pH to 7.4 with glacial acetic acid |
| Organic extraction | 2-butanol/suspension (v/v) |
| Acid precipitation | pH 6.2; 2 mM DTT; 0.1% SDS |
| Centrifugation | 10,000–15,000 × g |
| Acid precipitate solubilization | 2% SDS; 5 mM EDTA; 50 mM phosphate buffer |
| Reduction | 20 mM DTT; pH 8.5; heat to 50° for 10 min. under nitrogen; cool to about 25° C. |
| Sephacryl ® S-200 column | 50 mM acetate; pH 5.5; 1% SDS: 1 mM EDTA |
| Oxidation | Iodosobenzoic acid (IBA) equimolar; protein:IBA; 0.1% SDS; 2 mM sodium pyrophosphate; pH 9; 1 mM EDTA |
| Concentration | pH 5.5 |
| Sephacryl ® S-200 column | 50 mM acetate; pH 5.5; 0.1% SDS; 1 mM EDTA |
| Concentration | |
| Sephadex ® G-75 column | 50 mM acetate; pH 5.5; 0.1% SDS; 1 mM EDTA |
| Sephadex ® G-25 column | 1 mM NaOH |
| Stabilization | 1.25–5.00%; normal serum albumin |

| -continued | |
|---|---|
| PROTOCOL 1 | |
| Formulation | (human); pH 11 → 12.0 → 7.5 1.25% dextrose |
| Pre-filtration | 0.45 μM |
| Sterile filtration | 0.22 μM |
| Lyophilization | |
| Final Container Product | |

| PROTOCOL 2 | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15–23% sucrose (w/w) |
| Centrifugation | 10,000–15,000 × g |
| Paste solubilization | 1–2% sodium laurate, 20 mM phosphate buffer, 50 mM DTT, pH 9–10 (with sonication) |
| Reduction | 10 mM DTT; 1–2% sodium laurate; 2 mM EDTA; pH 9; heat to 50° C. for 10 min. under nitrogen; cool to about 25° C. |
| Sephacryl ® S-200 column | 10 mM Tris.HCl; pH 9.2; 1–2% sodium laurate; 1 mM EDTA |
| Oxidation | Iodosobenzoic acid (IBA) equimolar; protein:IBA; 1–2% sodium laurate; 2 mM sodium pyrophosphate; pH 9; 1 mM EDTA |
| Concentration | pH 9.0 |
| Sephacryl ® S-200 column | 10 mM Tris.HCl; pH 9.2; 0.1–0.5% sodium laurate; 1 mM EDTA |
| Concentration | 10 mM Tris.HCl, pH 9.2; 0.1–0.5% sodium laurate, 1 mM EDTA |
| Sephadex ® G-75 column | 10 mM Tris.HCl; pH 9.2; .1–.5% sodium laurate; 1 mM EDTA |
| Sephadex ® G-25 column | 0.1% laurate; 10 mM Tris.HCl; pH 9.2 |
| pH Adjustment | pH of eluate lowered quickly to 3 with 1.0 N HCl; sodium laurate precipitates |
| Centrifugation and Filtration | To remove precipitated sodium laurate |
| Stabilization | 0.15% Trycol LAL-12 added |
| Neutralization | pH raised to between 6.0 and 7.2 |
| Polyol addition | 5% dextrose |
| Pre-filtration | 0.45 μM |
| Sterile filtration | 0.22 μM |
| Lyophilization (immediate) | |
| Final Container Product | |

| PROTOCOL 3 | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15–23% sucrose (w/w) |
| Centrifugation | 10,000–15,000 × g |
| Paste solubilization | 2% SDS phosphate buffered saline |
| Reduction | 10 mM DTT; 2% SDS; 2 mM EDTA; pH 9; heat to 50° C. for 10 min. under nitrogen; cool to about 25° C.; adjust pH to 7.4 with glacial acetic acid |
| Organic extraction | 2-butanol/suspension (v/v) |
| Acid precipitation | pH 6.2; 2 mM DTT; 0.1% SDS |
| Centrifugation | 10,000–15,000 × g |
| Acid precipitate solubilization | 2% SDS; 5 mM EDTA; 50 mM |

-continued
PROTOCOL 3

| | |
|---|---|
| Reduction | phosphate buffer<br>20 mM DTT; pH 8.5; heat to 50°<br>for 10 min. under nitrogen; cool<br>to about 25° C. |
| Sephacryl ® S-200 column | 50 mM acetate; pH 5.5; 1% SDS;<br>1 mM EDTA |
| Oxidation | Iodosobenzoic acid (IBA) equimolar;<br>protein:IBA; 0.1% SDS;<br>2 mM sodium pyrophosphate; pH 9;<br>1 mM EDTA |
| Concentration | pH 5.5 |
| Sephacryl ® S-200 column | 50 mM acetate; pH 5.5; 0.1% SDS;<br>1 mM EDTA |
| Concentration | |
| Sephadex ® G-75 column | 50 mM acetate; pH 5.5; 0.1% SDS;<br>1 mM EDTA |
| Sephadex ® G-25 column | 0.1% sodium laurate (transfer<br>component) in 10 mM Tris-HCl,<br>pH 9.2 |
| pH Adjustment | pH of eluate lowered quickly<br>with 1.0 N HCl to pH 3; sodium<br>laurate precipitates |
| Centrifugation and Filtration | To remove the precipitated sodium laurate |
| Stabilization | 0.1% Plurafac C-17 added |
| Neutralization | pH raised to between 6.0 and 7.2 |
| Polyol addition | 5% dextrose |
| Pre-filtration | 0.45 µM |
| Sterile filtration | 0.22 µM |
| Lyophilization (immediate) | |
| Final Container Product | |

Below, listed under the heading *Alternative Downstream Purification Processes*, are eight preferred downstream process alternatives incorporating the RP-HPLC methods of this invention.

ALTERNATIVE DOWNSTREAM PURIFICATION PROCESSES

Process I

1. Resolubilized Acid Precipitate (RSAP)
2. Gel filtration, preferably S-200
3. Controlled oxidation, preferably with IBA
4. RP-HPLC
5. Removal of organic solvents, preferably by precipitating the IFN-$\beta$ protein, and recovery of the IFN-$\beta$, preferably, by resolubilizing it in an appropriate buffer
6. Gel filtration, preferably S-200
7. Formulation and optionally lyophilization

Process II

The same as Process I except that the controlled oxidation step is performed after step 5

Process III

1. RSAP
2. RP-HPLC
3. Removal of organic solvents and recovery of IFN-$\beta$ protein
4. Controlled oxidation
5. Gel filtration, preferably S-200
6. Formulation and optionally lyophilization

Process IV

The same as Process III except that the controlled oxidation step occurs prior to step 2, that is, oxidation precedes RP-HPLC.

Process V

1. RSAP
2. RP-HPLC
3. Removal of organic solvents and recovery of the IFN-$\beta$ protein
4. Controlled oxidation
5. Immunoaffinity purification step
6. Formulation and optionally lyophilization

Process VI

1. Solubilized particle paste from the abbreviated front-end process
2. Gel filtration, preferably by S-200
3. RP-HPLC
4. Removal of organic solvents and recovery of the IFN-$\beta$ protein
5. Controlled oxidation
6. Gel filtration, preferably S-200
7. Formulation and optionally lyophilization

Process VII

1. RSAP
2. Gel filtration, preferably S-200
3. Controlled oxidation
4. Gel filtration, preferably S-200
5. RP-HPLC
6. Removal of organic solvents and recovery of the IFN-$\beta$ protein
7. Gel filtration, preferably G-75
8. Formulation of optionally lyophilization

Process VIII

1. RSAP
2. Gel filtration, preferably S-200
3. Controlled oxidation
4. Gel filtration, preferably S-200
5. Gel filtration, preferably G-75
6. RP-HPLC
7. Removal of organic solvents and recovery of the IFN-$\beta$ protein
8. Formulation and optionally lyophilization For purposes of practicing the present invention, bacteria are the preferred microorganism hosts, with *E. coli* being the most preferred.

In general, the recovery, purification and formulation processes herein involve fermenting the host organisms transformed to express the IFN-$\beta$, disrupting the cell wall and cell membrane of the host organisms, separating the refractile material containing the recombinant IFN-$\beta$ from the rest of the cellular debris, solubilizing the refractile material in an aqueous buffer under reducing conditions, extracting the IFN-$\beta$ with 2-butanol or 2-methyl-2-butanol, subjecting the extracted IFN-$\beta$ to chromatographic purification, and then diafiltering or desalting, preferably desalting, the IFN-$\beta$ to remove the solubilizing agent, optionally using a suitable transfer component, and formulating the purified IFN-$\beta$ with human serum albumin with or without dextrose or human plasma protein fraction (PPF) as described in Ser. No. 923,425; or with non-ionic biodegradable polymeric detergents as described in Ser. No. 923,425.

Protocols 1-3 illustrate the processes in which the RP-HPLC methods can be incorporated from culturing microorganisms transformed to produce IFN-$\beta$ protein in an appropriate fermentation medium through the final steps wherein the purified IFN-$\beta$ protein is stabilized and may then be lyophilized into therapeutic formulations that can then be reconstituted at the clinician's option. A preferred process for recovering and purifying recombinant IFN-β comprises:

(a) recovering a refractile material containing microbially produced IFN-β from a host microorganism cell culture transformed to produce said protein by the steps of:
  1(a) disrupting the cell wall and cell membrane of the microorganism;
  2(a) removing greater than 99% by weight of the salts from said disruptate;
  3(a) redisrupting the desalted disruptate;
  4(a) adding a material to the disruptate to increase the density or viscosity of, or to create a density or viscosity gradient in, the liquid within the disruptate; and
  5(a) separating the refractile material from the cellular debris by high-speed centrifugation;
(b) solubilizing the recombinant IFN-β in the refractile material with an aqueous solution of a solubilizing agent which forms a water-soluble complex with the recombinant IFN-β, said solution containing a reducing agent;
(c) separating the recombinant IFN-β from the resulting solution in the presence of said reducing agent by gel filtration;
(d) oxidizing the product of step (c);
(e) purifying the oxidized product of step (d) by RP-HPLC using a bonded phase wide pore silica gel column and a solvent system containing acetonitrile as an organic modifier and an organic acid selected from either heptafluorobutyric acid (HFBA) or trifluoroacetic acid (TFA);
(f) removing the organic solvents from the product of step (e), recovering the IFN-β protein therefrom, and re-solubilizing the IFN-β protein in an appropriate buffer; and
(g) further purifying the product of step (f) by gel filtration.

Said process can further comprise the steps of formulating and optionally lyophilizing the product of step (g).

Preferably, the removal of the organic solvents and recovering the IFN-β protein in step (f) is accomplished by precipitating the IFN-β protein and then resolubilizing the protein. Preferably, such precipitation is accomplished by raising the pH and increasing the salt concentration. The salt concentration and pH are preferably raised by adding 3M sodium phosphate, pH 6, to the reverse-phase pool until a heavy precipitate forms.

Further preferred processes of the instant invention include those wherein the oxidizing step (d) of the above-described process is a controlled oxidation step carried out by using iodosobenzoic acid according to the method described in U.S. Pat. No. 4,530,787 to Shaked et al., herein incorporated by reference; or by using an oxidation promoter containing a $Cu^{+2}$ cation such as $CuCl_2$ according to the method described in U.S. Pat. No. 4,572,798 to Koths et al., also herein incorporated by reference. Preferably, the controlled oxidation step is carried out employing iodosobenzoic acid.

The gel filtration of steps (c) and (g) are preferably carried out on a S-200 column.

Process I

Another preferred purification process incorporating a RP-HPLC method option herein disclosed comprises, in addition to the process steps described immediately above, further process steps under (a) for recovering the refractile material. Those steps are as follows:
  6(a) solubilizing the refractile material under reducing conditions;
  7(a) organically extracting the solubilized refractile material; and
  8(a) isolating said refractile material from the extractant.

Step 8(a) is preferably carried out by employing an acid precipitation step followed by centrifugation. The process containing such steps is herein designated Process I.

Process II

Another preferred alternative process of this invention for purifying recombinant IFN-β includes the above-described steps respectively for the process designated Process I except that steps (e) and (f), the RP-HPLC step and organic solvent removal step, respectively, occur before step (d), the controlled oxidation step.

Process III

Another preferred alternative process includes all the steps in the order of Process II expect that step (c) (the first gel filtratio step) is omitted.

Process IV

Another preferred alternative process is similar to Process III except that the controlled oxidation step occurs before the RP-HPLC and removal of organic solvents.

Process V

Another preferred alternative process is similar to Process III except that an immunoaffinity purification step replaces the gel filtration step (g).

Process VI

Another preferred alternative process of this invention is similar to the steps of Process II except that steps 6(a), 7(a) and 8(a) of Process II are omitted.

Process VII

Another representative process of the present invention is similar to Process I except for the following differences: (1) there is an additional gel filtration step, preferably on an S-200 column, between the controlled oxidation step (d) and the RP-HPLC step (e); and (2) the last gel filtration step (g) is preferably carried out on a G-75 column.

Process VIII

Another preferred alternative process of this invention is similar to that of Process VII except that the third gel filtration step, preferably on a G-75 column, occurs prior to the RP-HPLC and removal of organic solvent steps rather than thereafter as in Process VII.

Preferred Version of Process I and, by Analogy, Processes II–VI

The steps of Process I and, by analogy, processes II–VI could preferably be carried out as follows:
(a) growing the transformed bacterial hosts in an appropriate fermentation medium;

(b) concentrating the bacteria in the fermentation medium by cross-flow filtration, centrifugation or other conventional methods;

(c) disrupting the cell wall and cell membrane of the bacteria;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate;

(g) separating the refractile material containing the IFN-$\beta$ protein from the cellular debris by high-speed centrifugation;

(h) solubilizing the refractile material in an aqueous buffer under reducing conditions;

(i) organically extracting the solubilized refractile material, preferably with 2-butanol or 2-methyl-2-butanol;

(j) isolating said refractile material from the extractant, preferably by employing an acid precipitation step followed by centrifugation;

(k) solubilizing the resulting IFN-$\beta$ particle pellet with distilled water or with an aqueous solution of SDS at a IFN-$\beta$ to SDS ratio of about 1:3, (l) adjusting the pH of the solution to about 9.5 and reducing the solubilized IFN-$\beta$;

(m) purifying the reduced IFN-$\beta$ by gel chromatography;

(n) collecting the eluted fraction of the purified IFN-$\beta$;

(o) oxidizing the eluate by a controlled oxidation method employing iodosobenzoic acid;

(p) purifying the oxidized product of step (o) by RP-HPLC using a bonded-phase, wide-pore silica gel column and a solvent system containing acetonitrile as an organic modifier and an organic acid selected form either HFBA or TFA;

(q) removing the organic solvents from the product of step (p) by precipitating the protein and thereafter recovering the protein by re-solubilizing it in an appropriate buffer;

(r) further purifying the IFN-$\beta$ by gel chromatography and collecting the eluate containing the purified IFN-$\beta$;

(s) desalting the purified IFN-$\beta$ eluate in a desalting column equilibrated and run in 0.1% sodium laurate in 10 mM Tris-HCl at pH 9.2;

(t) lowering the pH of the eluate quickly to pH 3.0 with an appropriate acidic agent;

(u) centrifuging and filtering the IFN-$\beta$ pool;

(v) adding an effective amount of a non-ionic biodegradable polymeric detergent-containing solubilizer/stabilizer;

(w) adjusting the pH of the solution of near physiological pH;

(x) adding an appropriate polyol bulking/stabilizing agent in a concentration of from about 0.25% to about 10%;

(y) filtering the solution;

(z) immediately lyophilizing the IFN-$\beta$ sample; and (a') reconstituting the lyophilized IFN-$\beta$ sample, if desired.

Ten mM dithiothreitol (DTT) may be optionally included in the initial solubilization step, and the mixture may be heated to about 50° C. for about 10 minutes. Preferably, 50 mM DTT can be included in said inital solubilization, and the mixture is heated to about 50° C. for about 20 minutes.

The IFN-$\beta$ is preferably oxidized in step (o) so that its cysteine residues are bridged to form cystines, as described by U.S. Pat. No. 4,530,787 to Shaked et al., using o-iodosobenzoic acid solution or by U.S. Pat. No. 4,572,798 to Koths et al. using copper chloride. Preferably, o-iodosobenzoic acid is employed for such a controlled oxication step.

Commonly owned, copending U.S. patent application Ser. Nos. 843,997 (filed Mar. 25, 1986) and 923,423 filed Oct. 27, 1986), details procedures for culturing a microorganism host transformed to produce IFN-$\beta$ and for extracting, purifying and formulating the recombinant protein. Said purification procedures are exemplary of the processes in which the RP-HPLC method of the present invention is incorporated. A synopsis of said procedures follows.

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp. 80–85 (1980).) In expression vectors involving the trp promoter, the tryptophan concentration in the medium is carefully controlled to become limiting at the time IFN-$\beta$ expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680nm), by cross-flow filtration, centrifugation, or other conventional methods. Preferably, a compound which is non-toxic to humans, such as 1-octanol, in an amount of about 1% by weight of total components, is added to the fermenter before or during cell concentration to ensure that no viable recombinant organisms remain before containment is broken.

Following concentration of the harvested culture, the cell membranes of the microorganisms are disrupted. Conventional cell disruption techniques such as homogenization, sonication, or pressure cycling may be used in this step of the process. Preferred methods are sonication or homogenization with a homogenizer. The end point of the disruption step can be determined by monitoring the optical density with the absorbance at 260 nm of the suspension typically increasing with cell lysis. In any event, the disruption should break substantially all of the cells so that substantially no intact cells are carried through to the solubilization step. Before the disrupting, the pH of the liquid phase of the concentrate is adjusted, if necessary, to a level that facilitates removal of *E. coi* proteins in subsequent steps, while retaining the heterologous protein as an insoluble complex in the cellular debris.

After the cells have been disrupted, deionized water is preferably added to the disruptate and greater than 99% by weight of the salts are removed therefrom. The removal of these salts to reduce the ionic strength of the disruptate may be accomplished by diafiltration using deionized water to flush out the ions or by centrifuging to pellet the cellular debris and refractile bodies followed by resuspension in deionized water.

After the salts are essentially removed, optionally a compound such as 1-octanol may be added to the desalted disruptate, if not added earlier, to ensure that no viable recombinant organisms remain. The desalted disruptate is again disrupted as described above for the initial disruption.

After redisruption, density or viscosity is increased and/or a gradient is created during centrifugation in the liquid within the disruptate by adding a material to the disruptate. One means to accomplish this goal is to add a material such as a sugar or mixture of sugars or a two-phase system, such as a glycerol/sugar mixture which increases the density of the liquid to a p of about 1.1 to 1.3 g/ml, preferably 1.13 to 1.17 g/ml. Also, the viscosity of the liquid phase may be increased to from 5 to 10 centipoise by any suitable means such as by adding a viscous compound such as, e.g., sucrose or glycerol thereto.

In the final step of the abbreviated "front-end" process to recover the refractile bodies, the refractile bodies containing the desired protein are separated from the cellular debris by high-speed centrifugation. By "high-speed centrifugation" is meant spinning the suspension in a centrifuge at about 10,000 to 40,000 times gravity, preferably about 10,000–20,000×g, for a suitable time period depending on the volume, generally about 10 minutes to seventy-two hours. The pellet resulting from the centrifugation is called the "particle pellet" or "particle paste." The abbreviated front-end process is most preferably used when sodium laurate is the primary solubilizing agent.

In an alternative, expanded "front-end" process to recover the refractile bodies, the particle pellet obtained from the last centrifugation step of the abbreviated front-end process is solubilized, reduced and then extracted from the aqueous medium with 2-butanol or 2-methyl-2-butanol. The extractnat phase is then precipitated with an acid and centrifuged to produce a "final pellet" or "final paste", which is then further purified as indicated.

The alternative, expanded front-end process is distinguished from the abbreviated front-end process in that it comprises several additional steps as follows0 solubilizing the refractile bodies under reducing conditions; organically extracting the solubilized refractile material; and isolating said refractile material from the extractant. Essentially, the enhanced purity of the final pellet as opposed to the particle pellet lessens the purifying burden of downstream processing. There is an interdependence between the choice of the front-end process and later process purification steps to achieve the desired purity level for the final product. Once the choice of the particular front-end recovery of the refractile bodies has been made, one skilled in the art can pick and choose the alternative purifying steps outlined below to achieve the desired purity level of the final product.

Whether the abbreviated or expanded front-end process is utilized to recover the refractile bodies containing the IFN-$\beta$, the next step is purification is solubilizing either the particle or final pellet containing the refractile material. The following solubilizing agents can be used: sodium dodecyl sulfate (SDS), sodium laurate, urea, sodium dodecyl sulfonate, sodium decyl sulfate, sodium tetradecyl sulfate, sodium tridecyl sulfonate, sodium dodecyl N-sarcosinate, sodium tetradecyl N-sarcosinate, sodium dioctylsulfosuccinate, and guanidine hydrochloride. Preferred solubilizing agents are SDS, sodium laurate or guanidine hydrochloride.

The solubilizing agent is in an aqueous buffer, preferably phosphate buffered saline. The preferred percentage of the solubilizing agent is in the range of 1% to 5% (w/v). (Percentages herein reflect weight to volume ratios.) The preferred solubilizing solutions are phosphate buffered saline with 1–2% sodium laurate (20 mM NaPO$_4$) at pH 9–10 and 1–5% SDS in 50 mM $\beta$-mercaptoethanol. Sonication is preferably employed when sodium laurate is employed as the solubilizing agent to promote solubilization.

Reducing agents that can be employed during the solubilization step include: $\beta$-mercaptoethanol ($\beta$-mer), glutathione, cysteine and dithiothreitol (DTT). DTT and $\beta$-mer are the most preferred reducing agents. It is preferred that reducing agents be employed when either sodium laurate or guanidine hydrochloride is used as the primary solubilizing agent.

The solubilization will typically be carried out at temperatures in the range of 20° C. to 25° C. with mixing to facilitate contact between the solid phase and the solubilizing medium. Optionally, a reduction step may be carried out at this point. The pH, if necessary, may be adjusted to a range of 8.5 to 10, most preferably approximately 9. The suspension may be heated to 50°±5° C. for 5 to 15 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

After the protein is solubilized, the resulting suspension may optionally be centrifuged at 10,000–40,000 ×g, preferably 10,000 to 15,000×g, to obtain a pellet containing, inter alia, additional host (e.g., *E. coli*) proteins, notably including certain contaminants that have molecular weights very close to that of the desired protein. The exact speed of centrifugation is not critical, as most of the insoluble material will come out, even at low speeds. The pellet is discarded and the supernatant containing the desired protein is retained and processed to recover the desired protein.

If a reduction step was not carried out during the solubilization, the next step in the process would be a reduction of the solubilized refractile body protein. A preferred reducing agent is dithiothreitol (DTT). Reduction conditions may also include the addition of a chelating agent such as ethylenediaminetetraacetic acid (EDTA).

The next step in the process is to separate the protein in the supernatant from any host contaminants remaining after the centrifugation or filtration and optimally from the solubilizing agent. According to this invention, as represented by preferred embodiments of the instant invention outlined above, combinations of gel filtration, RP-HPLC, and/or immunoaffinity chromatography can be used. [Immunoaffinity chromatography is described in Pestka et al., *Pharmac. Ther.*, 29: 299–319 (1985).] Gels that are capable of fractionating the solution to permit separation of the protein from these contaminants are commercially available. Sephacryl ® S-200 is a preferred gel for removing the higher molecular weight components, and Sephadex ® G-50, G-75 or G-100 gels are preferred for removing the low molecular weight contaminants. The gel filtrations will typically be run in buffered solutions (pH 5.5 to 7.0) containing about 0.1% to 1.5% solubilizing agent and about 0.5 to 10 mM reducing agent. The column will be sized to permit suitable resolution of the desired components.

RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration.

It is preferred in carrying out the process of this invention that the last step of purification before stabilization of the formulation is a desalting step employing a transfer component, such as sodium laurate at a pH range of about 8.5 to about 10. The purity of the protein after the chromatography step(s) is at least about 95% and higher, and usually at least about 98%. This highly pure material contains less than about 2 ng endotoxin, usually less than about 0.01 ng endotoxin per 100,000 units protein bioactivity.

The formulation of the protein may be carried out as a separate operation using purified, selectively oxidized protein or in an operation that is integrated with the purification of the selectively oxidized protein.

Conventional solid non-protein bulking/stabilizing agents that are used in pharmaceutical tablet formulation may be used as the carrier. These materials are water soluble, do not react with the IFN-$\beta$ protein, and are themselves stable. They are also preferably non-sensitive to water, that is, non-hygroscopic. Specific examples of candidate carriers include polyols, starches and starch hydrolysates derived from wheat, corn, rice, and potatoes, as well as micro-crystalline celluloses.

The unit dosage amounts, that is, about 0.125 to 2 mg, preferably 0.25 to 1 mg of the recombinant beta-interferon, are dispensed into containers, the containers are capped with a slotted stopper, and the contents are lyophilized using conventional freeze-drying conditions and apparatus.

The lyophilized, sterile product consists of a mixture of (1) recombinant beta-interferon; (2) carrier, preferably a polyol, and more preferably, dextrose or mannitol; (3) a stabilizer, preferably HSA, or a non-ionic biodegradable polymeric detergent, preferably Trycol LAL-12 or Plurafac C-17; and (4) a small amount of buffer that will provide a physiological pH when the mixture is reconstituted. The product may also contain a minor amount of a preservative to enhance chemical stability.

The lyophilized mixture may be reconstituted by injecting a conventional parenteral aqueous injection such as distilled water for injection, Ringer's solution injection, Hank's solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml, preferably 1 to 2 ml.

The reconstituted formulation prepared as described above is suitable for parenteral administration to humans or other mammals in therapeutically effective amounts (i.e., amounts which eliminate or reduce the patient's pathological condition) to provide therapy thereto. IFN-$\beta$ therapy is appropriate for anti-cancer, anti-viral and anti-psoriasis treatment.

Recombinant IFN-$\beta$ is a "lipophilic protein," a term used herein to refer to a protein which is not soluble or not readily soluble in an aqueous medium under ambient conditions of room temperature and atmospheric pressure at a pH of between about 6.5 and 7.8. The term "recombinant protein" refers to a protein which is produced by recombinant DNA techniques wherein generally DNA is inserted into a suitable expression plasmid which is inserted into a host organism not native to the DNA which is transformed to produce the heterologous protein. The host may be any organism foreign to the DNA, such as, e.g., bacteria, yeast, viruses and, mammals, among other types of cells. Preferably the host is microbial, and most preferably bacterial.

As used herein, the term "IFN-$\beta$" refers to $\beta$-interferon or $\beta$-interferon-like polypeptides produced by recombinant DNA techniques and whose amino acid sequence is the same as or similar or substantially homologous to the unglycosylated and/or glycosylated native $\beta$-interferon.

The precise chemical structure of the IFN-$\beta$ protein will depend on a number of factors. As ionizable amino and carboxyl groups are present in the molecule, a particular IFN-$\beta$ protein may be obtained as an acidic or basic salt, or in neutral form. All such preparations which retain their activity when placed in suitable environmental conditions are included in the definition of IFN-$\beta$ proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IFN-$\beta$ protein herein so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Most preferably the IFN-$\beta$ protein is unglycosylated IFN-$\beta$ which is produced by a microorganism that has been transformed with an IFN-$\beta$ gene or a modification of the IFN-$\beta$ gene that encodes a protein having: (a) an amino acid sequence that is at least substantially identical to the amino acid sequence of native IFN-$\beta$ and (b) biological activity that is common to native IFN-$\beta$. Substantial identity of amino acid sequence means the sequences are identical or differ by one or more amino acid alterations (deletions, additions, substitutions) that do not cause an adverse functional dissimilarity between the synthetic protein and the native IFN-$\beta$. Examples of such proteins are the IFN-$\beta$ proteins described in U.S. Pat. Nos. 4,518,584 and 4,588,585. Most preferably, the IFN-$\beta$ is IFN-$\beta_{ser17}$ wherein the cysteine residue at amino acid position 17 is replaced by a serine residue.

EXAMPLES

The following examples further illustrate the RP-HPLC method and recombinant IFN-β purification processes of the invention. These examples are not intended to limit the invention in any manner. In these examples all temperatures are in degrees Celsius unless otherwise indicated.

EXAMPLE 1

Representative Process for Purifying Recombinant IFN-β not Incorporating RP-HPLC This example provides a representative process for recovering, purifying and formulating microbially produced IFN-β wherein a RP-HPLC method of the present invention is not employed. This process employs the expanded front-end for recovering the refractile material containing the IFN-β protein and corresponds in outline to Protocol 3.

An analog IFN-β designated IFN-$β_{ser17}$ was recovered from E. coli. The amino acid sequence of this recombinant IFN-β is different from that of native human IFN-β in that the cysteine at position 17 has been changed to serine. The strain of IFN-$β_{ser17}$-producing E. coli (K12/MM294-1) carrying plasmid pSY2501 used in this example was deposited at the American Type Culture Collection on Nov. 18, 1983 under accession number 39,517. Said analog is described in U.S. Pat. Nos. 4,518,584 and 4,588,585 assigned to Cetus Corporation.

The E. coli thus transformed were grown in a 1000-liter fermentor at 37° C. The dissolved oxygen was maintained at about 40% by, as necessary; (1) increasing agitation; (2) adding air; and (3) adding oxygen.

Once the fermenter was filled with water to the operating volume, the following trace elements were added:

| | |
|---|---|
| $ZnSO_4.7H_2O$ | 72 mM |
| $MnSO_4.4H_2O$ | 30 μM |
| $CuSO_4.5H_2O$ | 3 μM |
| $Na_3$ citrate.$2H_2O$ | 1.5 mM |
| $KH_2PO_4$ | 21 mM |
| $(NH_4)_2SO_4$ | 72 mM |

The fermenter feed and addition vessels were then sterilized according to standard operating procedures. Then the following sterile additions were made:

| | |
|---|---|
| $MgSO_4.7H_2O$ | 20 mM |
| $FeSO_4.7H_2O$ | 100 μM |
| L-tryptophan | 70 mg/L |
| thiamine.HCl | 20 mg/L |
| glucose | 5 g/L |

The fermenter was cooled and inoculated with frozen or seed E. coli culture at 2 mg/L. A glucose feed was employed to maintain the glucose concentration between 5-10 g/L. At approximately 15 hours after fermentation was begun, the pH was adjusted with KOH to 6.8. Optical density measurements and residual glucose measurements on samples were taken at 14-16 hours and approximately one hour intervals thereafter.

Induction of IFN-$β_{ser17}$ production by depletion of L-tryptophan from the culture medium occurred at about $OD_{680}=10$ followed by the addition of casamino acids to a final concentration of 2% at $OD_{680}=15$. The cultures were harvested when glucose consumption reached $40\pm6$ g/l.

Cell Concentration and Cell Wall and Membrane Disruption

The refractile bodies containing the IFN-$β_{ser17}$ protein were then isolated. The harvested material was concentrated about 5-10 fold by circulating the harvest material under pressure through UF cross-flow filtration cartridges with a 100K molecular weight cutoff. Cells were disrupted by 3 passes through a Manton-Gaulin high-pressure homogenizer at 6,000 to 8,000 psig.

Diafiltration

EDTA was added to the disruptate to a final concentration of 5 mM. The suspension was then diafiltered against 5 volumes of deionized water.

Redisruption

EDTA was then added to a final concentration of 2 mM. Octanol was added to 1% (v/v) to kill any residual live bacteria in the diafiltered product. The suspension was redisrupted by passing it twice through the Manton-Gaulin high-pressure homogenizer at 6,000-8,000 psig.

Sucrose Suspension and Centrifugation

Sucrose was added to the redisruptate to a final concentration of 23% (wt/wt), creating a final density gradient between 1.1 and 1.25 g/ml. The mixture was centrifuged at 10,000 to 15,000×g, and the particle pellet or paste was collected. A temperature of at least 20° C. was maintained prior to and during centrifugation.

Particle Paste Solubilization and Reduction

The particle pellet was then solubilized in phosphate buffered saline with 2% SDS. Solid DDT and EDTA were added to a final concentration of 10 mM and 2 mM, respectively. The suspension was heated to $50\pm5°$ C. for 10 minutes under nitrogen. The reaction mixture was then cooled to approximately 25° C., and then the pH of the mixture was adjusted to 7.4.

Organic Extraction and Acid Precipitation

A volume of 2-butanol equal to the total volume of the suspension was measured. The suspension and organic solution were pumped separately but simultaneously at flow rates of 1.1 to 1.3 liters per minute through a static mixer and then into a continuous centrifuge (Westfalia at approximately 11,770×g) for phase separation. The 2-butanol-rich phase containing the IFN-$β_{ser17}$ was collected (Organic Extract).

The 2-butanol extract was mixed with 2.5 volumes of 0.1% SDS in phosphate-buffered saline. Solid DTT was added to a final concentration of 2 mM. The pH of the organic extract/buffer solutions was adjusted to $6.2\pm0.1$ with glacial acetic acid (Acid Precipitate).

Centrifugation

The mixture was then centrifuged (Sharples centrifuge at 13,200×g) for approximately 2-6 hours, the supernatant was decanted and the final pellet was then collected (Final Pellet) containing approximately 81% IFN-β. The final pellet containing the refractile material was then further purified by downstream processing.

Acid Precipitate Solubilization and Reduction (RSAP)

The final pellet was then re-suspended with 2% SDS in 50 mM phosphate buffer and 5 mM EDTA. Solid DDT was added to a final concentration of 20 mM, and the pH was adjusted to 8.5 with NaOH. The suspension was heated to $50\pm5°$ C. for 10 minutes under nitrogen, and then cooled to approximately 25° C. The pH was then adjusted to a pH of 5.5 with glacial acetic acid, and the solution was filtered through a 0.65 μm filter. At this point the IFN-β is in the form known as resuspended acid precipitate (RSAP).

S-200 Pre-Column

The filtrate was then processed by pre-column chromatography by loading a Sephacryl® S-200 column and collecting fractions into clean, depyrogenated vessls using an elution buffer that is composed of 50 mM acetate, pH 5.5, 1 mM EDTA and 1% SDS. The fractions containing the IFN-β monomer were pooled.

The pre-column pool was then concentrated by using a hollow-fiber ultrafiltration unit with a 10K molecular weight cut-off.

Oxidation Resulting in Oxidized Pre-column Pool

The concentrated pre-column pool was then oxidized using o-iodosobenzoic acid (IBA). The oxidation was effected by adding equimolar amounts of protein and IBA into a reaction vessel containing 2 mM sodium pyrophosphate, 0.1% SDS and 1 mM EDTA. A 20 μM excess of IBA was present at the end of the oxidation. The pH was controlled at 9.0±0.1 with NaOH during oxidation, and adjusted to 5.5±0.2 with glacial acetic acid when the oxidation was completed.

Concentration

The IFN-β protein was then concentrated using a hollow-fiber ultrafiltration unit with a 10K molecular weight cut-off.

S-200 Main Column

The protein was then loaded onto the main column (Sephacryl® S-200), and fractions were collected into clean, depyrogenated vessels using an elution buffer that is composed of 50 mM acetate, pH 5.5, 1 mM EDTA and 0.1% SDS.

A SDS-PAGE was performed on samples from each fraction tube starting from the beginning of the peak to be pooled to the end of the peak. Using the SDS-PAGE results, the fractions containing no high molecular weight contaminants were then pooled.

Concentration

The main column pool was then concentrated by using a hollow-fiber ultrafiltration unit with a 10K molecular weight cut-off.

G-75 Column

The above procedure performed with the main column was repeated on a Sephadex® G-75 column. Using the SDS-PAGE results, the fractions containing neither low nor high molecular weight contaminants were pooled.

G-25 Column and pH Adjustment

The desalting step was then performed at pH 9.2 wherein 0.1% sodium laurate was used as a transfer component as follows. The pH was adjusted with an appropriate basic agent such as 1 mM NaOH.

A Sephadex® G-25 column was then equibrated with 0.1% sodium laurate in 10 mM Tris-HCl, pH 9.2 and loaded with the Sephadex® G-75 pool containing 0.1% SDS. Using the process chromatogram, the IFN-$\beta_{ser17}$ peak was collected. The pH of the eluate was then lowered quickly with 1.0N HCl to pH 3.0, which precipitated the sodium laurate, but left the IFN-$\beta_{ser17}$ in solution.

Centrifugation and Filtration

The mixture was centrifuged at 35,000×g for 30 minutes and the supernatant was filtered through a 0.22 micron nitrocellulose filter. SDS concentration was assayed by acridine orange. [Sokoloff et al., "Rapid Spectrophotometric Assay of Dodecyl Sulfate Using Acridine Orange," Anal. Biochem., 118: 138–141 (1981).] The recovery of the G-25 pool was above 85%, and the SDS concentration was reduced to less than 10 μg/mg.

Formulation

The filtered supernatant was then stabilized by adding 0.15% Trycol LAL-12. The pH of the formulated product was then raised to about 7.0±0.3 with NaOH. The bulking/stabilizing agent, 5% dextrose, was then added. The solution was then pre-filtered and sterile filtered through 0.45 and 0.22 micron nitrocellulose filters, respectively. Immediately thereafter the correct dosage amounts of the IFN-$\beta_{ser17}$ 0.25 mg containing $0.5\times10^8$ units, were aseptically filled into sterilized vials with sterilized stoppers under sanitary and sterile conditions that were carefully monitored. The vials were then quickly placed in a lyophilizer where appropriate thermocouples were attached. The vials were frozen to between −35° and −45° C. The lyophilization cycle was completed, and the vials were mechanically sealed under a vacuum.

EXAMPLE 2

Reducing Levels of Microimpurities by RP-HPLC

Approximately 50 mg of IFN-β protein eluted from the G-25 column (see Example 1) was concentrated in a stirred Amicon cell to 17.4 mg/ml. A 3 ml aliquot (52.2 mg) was applied to a 22 mm $C_{18}$ column (Vydac 218TP, 15–20 micron particles) that had been equilibrated in 50% acetonitrile, 0.1% HFBA. The IFN-β protein was eluted with a linear gradient of a 0.33% increase in acetonitrile concentration per minute and with a flow rate of 15 ml/min. Half-minute fractions were collected, beginning at 30 minutes. The eluted fractions were analyzed in two ways: by Western blotting and by reinjection into an analytical $C_{18}$ column.

For Western blot analysis, fractions were evaporated to dryness in the presence of a small amount of SDS, using a Speed-Vac® concentrator, and resuspended in 1% SDS. The Western blots were run and developed for IFN-β (monoclonal a anti-IFN-β; 0.5 μg protein/lane) or E. coli (rabbit anti-E. coli protein; 10 μg protein/lane).

The Western blots of the IFN-β species in the various fractions wherein the samples were reduced (UREA/SDS-PAGE) or non-reduced (SDS-PAGE) indicated that the low molecular weight species were most concentrated in fractions from the trailing edge of the main peak (peak B); whereas oligomers were concentrated in fractions both from the leading and trailing edge of the main peak (peak B). The mid-peak fractions were relatively clean of oligomers.

Western blots were run of the E. coli species present in each fraction and the G-25 starting material. The amounts of E. coli protein species were so low, even in the G-25 material, that it was difficult to draw conclusions.

For analytical RP-HPLC analysis, aliquots containing approximately 20 μg of protein were reinjected on an analytical $C_{18}$ column (Vydac 218 TP, 5 micron particle size). The samples were eluted using a 50–65% linear gradient of acetonitrile/0.1% HFBA.

Peaks A and C on the chromatographs represent minor IFN-β species that are considered microimpurities whereas peak B contains the main IFN-β product.

The amounts of peaks A and B in each fraction and in the G-25 starting materials are listed in Table 1. The results indicate that the proportion of peak A decreases and the proportion of peak B increases progressively through the chromatogram.

TABLE 1

| | Peak A, Peak B, and Retention Time of the Major Peak in Each Fraction | | |
|---|---|---|---|
| Fraction | Peak A (%) (16–21 Minutes) | Peak B (%) (25.4–25.8 Minutes) | $T_R$ of Major Peak (Minutes) |
| G-25 (Concentrated to 17.2 mg/ml) | 6.1 | 58.5 | 25.6 |
| 32.5 Minutes | 99.8 | Below Detection Limit | 20.0 |
| 36.0 Minutes | 4.2 | Below Detection Limit | 24.5 |
| 38.0 Minutes | 2.1 | 49.8 | 25.4 |
| 39.0 Minutes | 0.3 | 69.4 | 25.4 |
| 40.0 Minutes | 0.3 | 98.7 | 25.4 |
| 42.0 Minutes | 0.3 | 97.7 | 25.6 |
| 45.5 Minutes | Below Detection Limit | 100.0 | 25.8 |

This example indicates that the RP-HPLC method gives a good separation of many of the IFN-$\beta$ species seen by both analytical RP-HPLC and by Western blotting. Compared to the G-25 starting material, the mid-peak fractions obtained by this RP-HPLC separation were reduced in peaks A, C and other species from the leading and trailing edges of peak B, as well as low molecular weight IFN-$\beta$ fragments and oligomers.

EXAMPLE 3

Purification of G-75 Pool IFN-$\beta$ by Preparative Scale RP-HPLC

This example indicates that when one-half gram of G-75 IFN-$\beta$ (see Example 1) was purified by a RP-HPLC method of this invention that the reverse phase pool contained approximately one-third as much peak A as the starting material and was reduced in peak C and other species detected by analytical RP-HPLC, as well as in the low molecular weight species and dimers detected by Western blotting.

Whereas Example 2, wherein 50 mg of G-25 IFN-$\beta$ was eluted over a $C_{18}$ column, represents an intermediate step in scaling up a RP-HPLC purification of IFN-$\beta$ to the preparative level, in this example, the RP-HPLC load was increased 10-fold to a load comparable to that which would be used in a preparative separation process. G-75 IFN-$\beta$ prepared according to Example 1 was used as the starting material.

The experiment was performed by first concentrating G-75 IFN-$\beta$ to 23.8 mg/ml in a stirred Amicon cell. Five aliquots of 5 ml each, totalling 476 mg of protein, were applied to a pre-packed Vydac 218TP1520 column ($C_{18}$, 15–20 micron particles) that had been equilibrated in 50% acetonitrile/0.1% HFBA. The elution was in a gradient of from 50% to 80% acetonitrile with a 0.33% increase in concentration of acetonitrile per minute and at a flow rate of 15 ml/min. Half-minute fractions were collected. Fractions taken at 5-minute intervals were analyzed by Western blotting and analytical RP-HPLC as described in Example 2.

To achieve a desired yield of 66% of the total amount of IFN-$\beta$ protein eluted, fractions from 55–80 minutes were pooled. The pooled fractions were analyzed by Western blotting and by analytical RP-HPLC using a computerized exponential skim integration method.

Recovery of protein as judged by $A_{280}$ readings was approximately 100%. The column was washed by applying 5 ml of 1% SDS and eluting with the same gradient. Only a very tiny peak of absorbance at 280 nm was eluted.

Table 2 summarizes and quantitates the results of the RP-HPLC analyses of the G-75 starting material, and of selected fractions.

TABLE 2

| | Analysis of Selected Fractions by RP-HPLC | | | |
|---|---|---|---|---|
| Fraction (Minutes) | Peak A (%) (18–20 Minutes) | Between A & B (%) (20.1–24.9 Minutes) | Peak B (%) (25–26.5 Minutes) | "Post B" (%) (26.5+ Minutes) |
| G-75 IFN-$\beta$ DC-100 Conc. G-75 | 1.4 | 1.5 | 97.1 | — |
| IFN-$\beta$, DC-100 | 1.5 | 2.0 | 96.5 | — |
| 32.5 | 3.3 | 76.3 | 14.7 | 5.8 |
| 37.5 | 2.9 | 96.5 | — | 0.6 |
| 42.5 | 17.6 | 82.5 | — | 0.2 |
| 47.5 | 3.6 | 19.2 | 77.0 | 0.1 |
| 52.5 | 0.5 | 2.8 | 96.7 | — |
| 57.5 | — | 1.2 | 98.4 | 0.4 |
| 62.5 | — | 1.0 | 98.3 | 0.7 |
| 67.5 | 0.2 | 0.7 | 98.2 | 0.9 |
| 72.5 | — | — | 100.0 | — |
| 77.5 | — | — | 100.0 | — |
| 82.5 | — | — | 97.2 | 2.8 |
| 87.5 | — | 27.9 | 72.1 | — |
| 92.5 | 3.9 | 37.0 | 51.6 | 7.5 |
| 96.5 | — | — | — | 100.0 |
| 97.5 | — | — | — | 100.0 |

As the results in Table 2 show, there is a progressive decrease in the amount of peak A and a corresponding increase in the percentage of peak B in the fractions collected from 42.5–82.5 minutes, as well as a rise in the quantity of "post B" species in the 82.5 minute fraction.

Western blots for IFN-$\beta$ protein indicated that the low molecular weight IFN-$\beta$ species are concentrated in fractions from 37–47 minutes. Whereas said blots indicated that dimers and higher molecular weight IFN-$\beta$ species are concentrated in both the earlier and later fractions, the fractions from the mid-portion of the chromatogram are reduced in these species. No separation of the high molecular weight IFN-$\beta$ band from the main band of IFN-$\beta$ monomer was achieved.

A Western blot for *E. coli* fractions indicated that these proteins appear to be concentrated in the early fractions, while none were detected in fractions from 52 minutes and later. It was, however, difficult to draw conclusions, in that the levels of the *E. coli* proteins were so low in the starting material.

Fractions from 55–80 minutes were pooled to give a yield of 66% of the eluted protein. RP-HPLC analysis of the pooled fractions and starting material indicated that the pooled material from the RP-HPLC column was reduced in peak A as compared to the G-75 IFN-$\beta$.

The amounts of peak A, peak B, and other species, as quantified by a computerized exponential skim integration, are listed in Table 3, below.

TABLE 3

Analysis of Pooled Fractions by RP-HPLC

| Sample | Peak A (%) (30.0–30.1 Minutes) | Peak B (%) (32.5–32.6 Minutes) | Other Species (%) |
|---|---|---|---|
| G-75, DC-100 (3.13 mg/ml) | 2.8 | 92.1 | 5.1 |
| Conc. G-75, DC-100 (23.8 mg/ml) | 9.2 | 82.8 | 8.0 |
| RP Pool[1] (1.51 mg/ml) | 0.9 | 95.2 | 3.9 |

[1]Fractions from 55–80 minutes were pooled. Yield = 66.6%
The pooled fractions from the RP-HPLC elution contain approximately one-third the amount of peak A, as does the G-75 IFN-$\beta$, and are reduced in other minor species of IFN-$\beta$. Further, Western blots showed that the the pooled fractions contain less of the low molecular weight species and dimers of IFN-$\beta$ than does the G-75 IFN-$\beta$.

The pooled fractions from the RP-HPLC elution contain approximately one-third the amount of peak A, as does the G-75 IFN-$\beta$, and are reduced in other minor species of IFN-$\beta$. Further, Western blots showed that the pooled fractions contain less of the low molecular weight species and dimers of IFN-$\beta$ than does the G-75 IFN-$\beta$.

EXAMPLE 4

Preparative Scale RP-HPLC Run of Oxidized Pre-Column Pool IFN-$\beta$

This example indicates that a preparative-scale RP-HPLC separation of oxidized pre-column pool (see Example 3) on a 22 mm $C_{18}$ column, wherein the solvent system is acetonitrile/0.1% HFBA in a linear gradient, results in separations of peak A and other species detected by analytical RP-HPLC and of low molecular weight fragments, dimers, and oligomers seen by Western blotting. The elution patterns of these species are similar to the elution patterns seen with G-75 IFN-$\beta$ (see Example 3), which is a more pure starting material.

The experiment was performed by first filtering the oxidized pre-column IFN-$\beta$, prepared according to the procedures of Example 1, through a 0.45 micron filter. Then, 750 mg of the filtered, oxidized pre-column pool was pumped onto a pre-packed Vydac 218TP152022 column (C18, 22 mm diameter, 15–20 micron particles) that had been equilibrated in 50% acetonitrile/0.1% HFBA. IFN-$\beta$ was eluted with a biphasic solvent gradient wherein solvent A was 0.1% HFBA in water and solvent B was 0.1% HFBA in acetonitrile in a gradient from 50% to 100%. The flow rate was 15 ml/min. Recovery of the IFN-$\beta$ protein, as measured by absorbance at 280 nm, was approximately 75%.

Fractions were collected at half-minute intervals. Specific activities of such fractions were determined by the cytopathic effect (CPE) assay according to Steward, W. E., The Interferon System (New York: Springer-Verlag 1981) at page 17, and the results are listed below in Table 4 for fractions collected at five-minute intervals.

TABLE 4

IFN-$\beta$ Activity of Fractions from RP-HPLC of Oxidized Pre-Column Pool

| Fraction | Specific Activity[1] (U/mg) |
|---|---|
| Ox. Pre-Column Starting Material | $8.4 \times 10^6$ |
| 30 | — |
| 40 | — |
| 50 | — |
| 60 | $8.0 \times 10^4$ |
| 70 | $7.0 \times 10^6$ |
| 80 | $5.0 \times 10^7$ |
| 90 | $1.4 \times 10^8$ |
| 100 | $2.0 \times 10^8$ |
| 110 | $1.8 \times 10^8$ |
| 120 | $1.7 \times 10^7$ |
| 130 | $2.4 \times 10^8$ |
| 140 | $3.3 \times 10^8$ |
| 150 | $3.3 \times 10^8$ |
| 160 | $3.5 \times 10^8$ |
| 170 | $6.5 \times 10^7$ |
| 180 | $7.7 \times 10^7$ |

[1]CPE assay. All samples done in triplicate.

Table 4 indicates that fractions from the middle of the chromatogram are approximately an order of magnitude more active than the starting material, whereas the specific activities of the early and late fractions are less than or equal to that of the starting material. According to the CPE assay, approximately 700% of the original IFN-$\beta$ activity was recovered.

Selected fractions were analyzed by sodium dodecyl sulfate polyacrylamide gel electrophoresis (SDS-PAGE) and Western blotting.

For Western blot analysis, fractions collected at five-minute intervals were evaporated to dryness in the presence of a small amount of SDS, using a Speed-Vac ® concentrator, and resuspended in 1% SDS. Western blotting was performed with monoclonal anti-IFN-$\beta$ [(0.2 µg protein/lane); reduced samples (UREA/SDS-PAGE) and non-reduced samples (SDS-PAGE)] and with polycolonal anti-E. coli proteins (10 µg protein/lane). In the former blots for IFN-$\beta$ protein a high molecular weight IFN-$\beta$ band was detected throughout the chromatogram, although it appeared more concentrated in the early fractions. The middle fractions contain the lowest amounts of impurities, lower and higher molecular weight species and dimers.

In the latter Western blot for E. coli proteins, the amounts of E. coli proteins were quite low in some of the middle fractions.

RP-HPLC analyses of fractions collected at five-minute intervals were performed by reinjecting aliquots containing approximately 20 µg of protein onto an analytical $C_{18}$ column (Vydac 218 TP, 5 micron particle size). The samples were eluted using a 50–65% linear gradient of acetonitrile/0.1% HFBA. For comparison, G-75 IFN-$\beta$ prepared according to Example 1 and the oxidized pre-column pool starting material for this example were also analyzed. The analytical RP-HPLC results are summarized quantitatively in Table 5.

TABLE 5

Amounts of Peak A and Peak B in Fractions from the RP-HPLC of 750 mg Oxidized Pre-Column Pool on a 22 mm $C_{18}$ Column

| Fraction | Peak A (%) (17.2–19.6 Minutes) | Peak B (%) (23.0–25.0 Minutes) |
|---|---|---|
| G-75, DC-100 | 3.1 | 93.4 |
| Ox. P.C., BC-203 | 2.1 | 82.6 |
| 55 | 16.5 | — |
| 65 | 41.3 | — |
| 75 | 9.6 | — |

TABLE 5-continued

Amounts of Peak A and Peak B in Fractions from the RP-HPLC of 750 mg Oxidized Pre-Column Pool on a 22 mm $C_{18}$ Column

| Fraction | Peak A (%) (17.2–19.6 Minutes) | Peak B (%) (23.0–25.0 Minutes) |
| --- | --- | --- |
| 85 | — | — |
| 95 | 0.4 | 92.0 |
| 105 | 0.4 | 94.2 |
| 115 | 0.6 | 94.0 |
| 125 | 0.6 | 94.8 |
| 135 | 0.7 | 90.8 |
| 145 | 1.9 | 85.8 |
| 155 | 1.5 | 64.9 |
| 165 | 2.4 | — |
| 175 | 14.8 | — |

The analytical RP-HPLC and Western blots indicated that the preparative-scale RP-HPLC separation of oxidized pre-column pool on a 22 mm $C_{18}$ column results in separations of peak A and other species detected by RP-HPLC and of low molecular weight fragments, dimers and oligomers seen by Western blotting. Very early fractions are enriched in peak A and species that elute between peak A and B, whereas late fractions are enriched in post-peak B IFN-$\beta$ species. The elution patterns of these species are similar to the elution patterns with G-75 IFN-$\beta$, a purer starting material. Further, the separation of the high molecular weight IFN-$\beta$ band detected throughout the chromatograph for the RP-HPLC treated material was not seen when G-75 IFN-$\beta$ was used as the starting material.

Further, the Western blot for *E. coli* proteins indicated that the preparative scale RP-HPLC of the oxidized pre-column pool, representative of the improved RP-HPLC methods disclosed herein, also separated *E. coli* proteins.

EXAMPLE 5

Purification of Resuspended Acid Precipitate (RSAP) by Preparative Scale RP-HPLC and S-200 Gel Filtration This example demonstrates that an alternative purification process comprising the application of preparative amounts of resuspended acid precipitate (RSAP; see Example 1) on a 22 mm $C_{18}$ column followed by oxidation of the reverse phase pool and further purification on a S-200 main column, results in a product having a level of *E. coli* proteins comparable to that of the G-75 IFN-$\beta$ (see Example 1) and also a reduction in the proportion of peak A species. Therefore, such a combination of RP-HPLC and S-200 gel filtration results in a more efficient process than that detailed in Example 1 and a purer product. This example also shows that the RP-HPLC method can handle a full preparative equivalent load of RSAP on a $C_{18}$ column, provided the size of the load and the slope of the elution gradient are balanced.

The experiment was performed by applying 800 mg of the RSAP, prepared according to Example 1, to a 22 mm $C_{18}$ column equilibrated in 50% acetonitrile/0.1% HFBA starting buffer.

The column was washed with starting solvent and then eluted with a linear gradient frm 50–65% acetonitrile/0.1% HFBA. Because of the size of the load, the slope of the elution gradient was greatly reduced as compared to runs wherein less material was loaded on the reverse phase column. The slope of the elution gradient, instead of being, for example, a 0.1% increase per minute for a 580 mg load of RSAP, was, in this experiment, a 0.04% increase in acetonitrile concentration per minute.

Fractions from the reverse phase column were evaluated by silver stained SDS Phast gels and by Western blotting for *E. coli* proteins. The levels of *E. coli* proteins at this point were shown to be comparable to levels wherein the load of RSAP was smaller but the slope of the elution gradient was steeper as indicated above.

The run was completed by further purification on a S-200 main column. Protein from the reverse phase pool was precipitated, resolubilized at a concentration of 0.25 mg/ml, and oxidized by the $CuCl_2$ method described in U.S. Pat. No. 4,569,790. The oxidized material was then eluted on an S-200 main column.

The S-200 column fractions were examined by silver stained SDS Phast gels and pooled to eliminate those fractions that were highest in the high molecular weight IFN-$\beta$ monomer. Pools from each stage of the process were examined by Western blotting for IFN-$\beta$ and *E. coli* proteins and by analytical RP-HPLC.

A comparison by analytical RP-HPLC of the S-200 pool from the test process with a sample of G-75 IGN-$\beta$ prepared according to Example 1 indicates that the material from the test process is clearly lower in peak A. The overall purity of the test process material, reported in Table 6, is increased from 92% to 99% peak B, according to a tangential skim analysis from the analytical RP-HPLC chromatograms.

TABLE 6

| Sample | Levels of Peak A and Peak B | |
| --- | --- | --- |
|  | Peak A (%) | Peak B (%) |
| S-200 Pool, Test Process | 0.9 | 99.1 |
| G-75 | 4.2 | 92.1 |

Western blots of both reduced and non-reduced samples from the test process for IFN-$\beta$ proteins indicated that the S-200 pool is lower in dimers than the G-75 material produced according to Example 1.

The Western blots for *E. coli* proteins, both from the S-200 pool of the test process and from the G-75 pool of Example 1, were both so low in *E. coli* proteins as to make comparisons difficult. Thus, the test process was confirmed in producing a product with very low amounts of *E. coli* proteins. A conclusion from this experiment was that balancing the amount of material loaded on the reverse phase column with the slope of the elution gradient purification processes of this invention results in a product which has therapeutically acceptable levels of *E. coli* proteins.

Conclusion

In summary, it can be seen that the RP-HPLC methods herein described provide a new and effective means of purifying recombinantly produced IFN-$\beta$. Benefits of such RP-HPLC purification method include the removal of non-IFN-$\beta$ protein and bacterial endotoxins and the reduction in levels of minor IFN-$\beta$ species. Further, purification processes incorporating a RP-HPLC method option of this invention either as an addition to other purification steps or as an alternative to one or more of such purification steps can result in very effective and efficient processes for purifying recombinant IFN-$\beta$.

The benefits of the alternative downstream purification processes herein described for IFN-$\beta$ include simplification of the downstream purification process; reduction in downstream process time; good reliability in terms of bacterial endotoxin removal; a process that can be reproducibly scaled-up; and a very pure IFN-$\beta$ product with reduced levels of minor IFN-$\beta$ species.

Modifications of the above-described modes for carrying out the invention which are obvious to those skilled in the fields encompassed by this disclosure and related fields are intended to be within the scope of the appended claims.

Deposits

As mentioned above, a culture of *E. coli* K12/MM294-1 carrying plasmid pSY2501 was deposited at the American Type Culture Collection 12301 Parklawn Drive, Rockville, MD 20852, U.S., on Nov. 18, 1983 under ATCC No. 39,517.

Said deposit was made pursuant to a contract between the ATCC and the assignee of this patent application, Cetus Corporation. The contract with the ATCC provides for permanent availability of said strain and progeny thereof to the public upon issuance of a U.S. patent related to this application describing and identifying the deposit or upon the publication or laying open to the public of any U.S. or foreign patent application, whichever comes first, and for the availability of the strain and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The deposit agreement under the terms of the Budapest Treaty assure that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of the deposited strain is not to be construed as a license to practice the invention in contravention of the rights granted under the authority of any government in accordance with its patent laws.

Also, the present invention is not to be considered limited in scope by the strain deposited, since the deposited embodiments are intended only to be illustrative of particular aspects of the invention. Any microoganism strain which is functionally equivalent to those deposited are considered to be within the scope of this invention. Further, various modifications of the invention in addition to those shown and described herein apparent to those skilled in the art from the preceding description are considered to fall within the scope of the appended claims.

What is claimed is:

1. A method for purifying recombinant interferon-$\beta$ (IFN-$\beta$) which comprises isolating the IFN-$\beta$ from hosts transformed to produce it and passing the isolated IFN-$\beta$ through at least one bonded-phase, wide-pore, silica gel, reverse-phase high performance liquid chromatography column using a solvent system comprising an organic modifier comprising from about 50% to 100% acetonitrile and an organic acid selected from the group consisting of heptafluorobutyric acid (HFBA) and trifluoroacetic acid (TFA).

2. A method according to claim 1 wherein the column is an alkane reverse phase column.

3. A method according to claim 2 wherein said alkane column is a $C_4$, $C_8$ or $C_{18}$ column.

4. A method according to claim 1 wherein the concentration (v/v) of HFBA or TFA is from about 0.001% to about 2%.

5. A method according to claim 4 wherein the concentration (v/v) of HFBA or TFA is from about 0.05% to about 1%.

6. A method according to claim 5 wherein the concentration of acetonitrile is from about 50% to about 65%.

7. A method according to claim 6 wherein the concentration (v/v) of HFBA or TFA is from about 0.1% to about 0.2%.

8. A method according to claim 7 wherein the gradient is linear and the slope of said gradient is balanced with the amount of material containing recombinant IFN-$\beta$ loaded on the reverse phase column.

9. A method according to claim 4 wherein the column is $C_{18}$ and the acid is HFBA.

10. A method according to claim 7 wherein the column is $C_{18}$ and the acid is HFBA.

11. A method according to claim 4 wherein the column is $C_4$ and the acid is TFA.

12. A method according to claim 7 wherein the column is $C_4$ and the acid is TFA.

13. A process for recovering and purifying microbially produced interferon-beta (IFN$\beta$) comprising:
   (a) disrupting the cell wall and cell membrane of a host microorganism cell culture transformed to produce said IFN-$\beta$;
   (b) removing greater than 99% by weight of the salts from said disruptate;
   (c) redisrupting the desalted disruptate;
   (d) adding a material to the disruptate to increase the density or viscosity of, or to create a density or viscosity gradient in, the liquid within the disruptate;
   (e) recovering refractile material containing the IFN-$\beta$ by high-speed centrifugation:
   (f) solubilizing the IFN-$\beta$ in the refractile material with an aqueous solution of a solubilizing agent which forms a water-soluble complex with the recombinant IFN-$\beta$, said solution containing a reducing agent;
   (g) oxidizing the product of step (f);
   (h) passing the oxidized product of step (g) through a bonded-phase wide-pore, silica gel, reverse-phase high performance liquid chromatography column using a solvent system comprising from about 50% to 100% acetonitrile and an organic acid selected from heptafluorobutyric acid (HFBA) and trifluoroacetic acid (TFA);
   (i) removing the solvent system from the product of step (h), recovering the IFN-$\beta$ protein therefrom, and resolubilizing the IFN-$\beta$ protein in a {an appropriate} buffer; and
   (j) further purifying the product of step (i).

14. A process according to claim 13 wherein the oxidizing step (g) is a controlled oxidation step carried out by using iodosobenzoic acid or by using an oxidation promoter containing a $Cu^{2+}$ cation.

15. A process according to claim 14 wherein the oxidation promoter containing a $Cu^{2+}$ cation is $CuCl_2$ and after step (f) and before step (g) the IFN-$\beta$ is separated from the resulting solution in the presence of said reducing agent.

16. A process according to claim 15 wherein the gel filtration in steps (g) and (h) is carried out on a S-200 column.

17. A process according to claim 14 further comprising after step (e) and before step (f) the steps of:
- (e') solubilizing the refractile material under reducing conditions;
- (e'') extracting the solubilized refractile material with an organic solvent; and
- (e''') isolating said refractile material from the extractant.

18. A process according to claim 17 wherein step (e''') is carried out by employing an acid precipitation step followed by centrifugation.

19. A process according to claim 17 wherein the solvent system is removed in step (i) by precipitating the IFN-$\beta$ protein.

20. A process according to claim 19 wherein the IFN-$\beta$ protein is precipitated by raising the pH and increasing the salt concentration of the product of step (h) until a heavy precipitate forms.

21. A process according to claim 20 wherein the salt concentration is increased by adding 3M sodium phosphate at pH 6.

22. A process according to claim 13 wherein the bonded phase, wide-pore, silica gel column is an alkane reverse phase column.

23. A process according to claim 22 wherein said alkane column is a $C_4$, $C_8$ or $C_{18}$ column.

24. A process according to claim 23 wherein the concentration (v/v) of HFBA or TFA is from about 0.001% to about 2%.

25. A process according to claim 24 wherein the concentration of acetonitrile is from about 50% to about 65% and wherein the concentration of (v/v) of HFBA or TFA is from about 0.1% to about 0.2%.

26. A process according to claim 25 wherein the column is $C_{18}$ and the acid is HFBA.

27. A process according to claim 26 wherein the column is $C_4$ and the acid is TFA.

28. A process according to claim 17 wherein steps (e) and (f) occur before step (d).

29. A process according to claim 15 wherein the step after step (f) and before step (g) is carried out by gel filtration and step (j) is carried out by gel filtration or by an immuno-affinity purification step.

30. A process according to claim 17 further comprising a gel filtration step between step (g) and step (h).

31. A process according to claim 29 wherein the gel filtration after step (f) and before step (g) and the gel filtration between steps (g) and (h) are carried out on S-200 columns, whereas step (g) is carried out by gel filtration on a G-75 column.

32. A process according to claim 31 wherein step (j) is carried out prior to step (h) and (i).

33. A process according to claim 13 further comprising the steps of stabilizing, and formulating the purified IFN-$\beta$ protein.

34. A process according to claim 33 further comprising the step of lyophilizing the formulated IFN-$\beta$ protein.

* * * * *

UNITED STATES PATENT AND TRADEMARK OFFICE
CERTIFICATE OF CORRECTION

PATENT NO. : 4,894,330

DATED : January 16, 1990

INVENTOR(S) : Susan Hershenson and Ze'ev Shaked

It is certified that error appears in the above-identified patent and that said Letters Patent is hereby corrected as shown below:

TITLE PAGE:
In the listing of Attorney, Agent, or Firm, please delete "Janet E. Hasak", and insert therefor --Leona L. Lauder--.

In the Abstract, line 2, please delete "betainterferon", and insert therefor --beta-interferon--.

Column 10, line 28, please delete "filtratio", and insert therefor --filtration--.

Column 11, line 25, please delete "1:3,", and insert therefor --1:3;--.

Column 11, line 67, please delete "." after "°C".

Column 12, line 9, please delete "oxication", and insert therefor --oxidation--.

Column 13, line 47, please delete "follows0", and insert therefor --follows:--.

Column 14, line 24, please delete "." after "°C", both occurrences.

Column 14, line 29, please delete "." after "°C".

Column 18, line 30, p

Signed and Sealed this

Seventh Day of May, 1991

Attest:

HARRY F. MANBECK, JR.

Attesting Officer

Commissioner of Patents and Trademarks